US008158439B2

(12) United States Patent
Shibata

(10) Patent No.: US 8,158,439 B2
(45) Date of Patent: Apr. 17, 2012

(54) MULTIPLE OPERATING MODE SAMPLE ANALYZER, ANALYZING METHOD, AND COMPUTER PROGRAM PRODUCT

(75) Inventor: Masaharu Shibata, Kobe (JP)

(73) Assignee: Sysmex Corporation, Kobe (JP)

( * ) Notice: Subject to any disclaimer, the term of this patent is extended or adjusted under 35 U.S.C. 154(b) by 699 days.

(21) Appl. No.: 12/218,607

(22) Filed: Jul. 16, 2008

(65) Prior Publication Data

US 2009/0035873 A1 Feb. 5, 2009

(30) Foreign Application Priority Data

Jul. 31, 2007 (JP) ................................. 2007-198681

(51) Int. Cl.
*G01N 1/10* (2006.01)
*G01N 15/12* (2006.01)
*G01N 15/14* (2006.01)
*G01N 35/00* (2006.01)
*G01N 33/49* (2006.01)
*G01N 21/05* (2006.01)
*G01N 21/85* (2006.01)

(52) U.S. Cl. .............. 436/179; 422/63; 422/64; 422/65; 422/67; 422/73; 436/43; 436/50; 436/55; 436/63; 436/66; 436/180

(58) Field of Classification Search .................... 422/67, 422/73, 514, 63–65; 436/43, 63, 179–180, 436/50, 55, 66
See application file for complete search history.

(56) References Cited

U.S. PATENT DOCUMENTS

| 3,523,733 | A | * | 8/1970 | Negersmith et al. ......... 324/71.4 |
| 3,567,390 | A | * | 3/1971 | Kling et al. .................... 422/501 |
| 3,578,039 | A | * | 5/1971 | Marbach ......................... 141/18 |
| 3,858,450 | A | * | 1/1975 | Jones ......................... 73/863.72 |
| 3,963,148 | A | * | 6/1976 | Proni et al. ..................... 222/132 |
| 3,976,429 | A | * | 8/1976 | Ginsberg ......................... 422/73 |
| 3,991,055 | A | * | 11/1976 | Godin et al. .................. 436/180 |
| 4,030,888 | A | * | 6/1977 | Yamamoto et al. ............. 422/67 |
| 4,068,169 | A | * | 1/1978 | Angel et al. .................. 324/71.1 |
| 4,086,631 | A | * | 4/1978 | Vick ............................... 436/66 |
| 4,099,917 | A | * | 7/1978 | Kim ................................ 436/10 |
| 4,152,391 | A | * | 5/1979 | Cabrera .......................... 422/82 |
| 4,157,499 | A | * | 6/1979 | Kacerek .......................... 377/12 |
| 4,206,504 | A | * | 6/1980 | Frey ................................ 436/66 |
| 4,220,621 | A | * | 9/1980 | Simpson et al. ................ 422/63 |
| 4,333,356 | A | * | 6/1982 | Bartels et al. ............... 73/864.21 |
| 4,387,076 | A | * | 6/1983 | Cabrera et al. .................. 422/67 |
| 4,606,631 | A | * | 8/1986 | Anno et al. ...................... 356/39 |

(Continued)

FOREIGN PATENT DOCUMENTS

JP 11-183472 7/1999

*Primary Examiner* — Arlen Soderquist
(74) *Attorney, Agent, or Firm* — Brinks Hofer Gilson & Lione

(57) ABSTRACT

The present invention is to present a sample analyzer which is automated even when measuring a small amount sample and is capable of improving a measurement precision. The sample analyzer S comprises a sample preparation section for preparing a measurement sample; a detector D3 for detecting an analyte contained in the measurement sample; and a controller 100 being configured to 1) control the sample preparation section so as to prepare a first measurement sample of a first dilution ratio, when measuring an ordinary amount sample; and 2) control the sample preparation section so as to prepare a second measurement sample of a second dilution ratio higher than the first dilution ratio, when measuring a small amount sample.

16 Claims, 12 Drawing Sheets

U.S. PATENT DOCUMENTS

| | | | | |
|---|---|---|---|---|
| 4,683,212 A | * | 7/1987 | Uffenheimer | 436/52 |
| 4,706,207 A | * | 11/1987 | Hennessy et al. | 702/21 |
| 4,726,237 A | * | 2/1988 | Yung | 73/864.83 |
| 4,727,033 A | * | 2/1988 | Hijikata et al. | 436/69 |
| 4,729,876 A | * | 3/1988 | Hennessy et al. | 422/539 |
| 4,948,565 A | * | 8/1990 | Bemis et al. | 422/501 |
| 4,957,008 A | * | 9/1990 | Proni et al. | 73/864.83 |
| 5,089,234 A | * | 2/1992 | Preston | 422/501 |
| 5,254,313 A | * | 10/1993 | Kuroda et al. | 422/514 |
| 5,256,573 A | * | 10/1993 | Kuroda et al. | 436/179 |
| 5,260,027 A | * | 11/1993 | Kuroda | 422/81 |
| 5,266,269 A | * | 11/1993 | Niiyama et al. | 422/73 |
| 5,270,212 A | * | 12/1993 | Horiuchi et al. | 436/45 |
| 5,287,733 A | * | 2/1994 | Oku et al. | 73/64.56 |
| 5,351,118 A | * | 9/1994 | Spinell | 356/72 |
| 5,380,491 A | * | 1/1995 | Carver et al. | 422/73 |
| 5,390,552 A | * | 2/1995 | Demachi et al. | 73/863.73 |
| 5,512,248 A | * | 4/1996 | Van | 422/501 |
| 5,631,165 A | * | 5/1997 | Chupp et al. | 436/43 |
| 5,728,351 A | * | 3/1998 | Carver, Jr. | 422/73 |
| 5,731,211 A | * | 3/1998 | Ohlin | 436/179 |
| 5,882,599 A | * | 3/1999 | Gilbert | 422/509 |
| 6,066,298 A | * | 5/2000 | Fukunaga | 422/510 |
| 6,098,471 A | * | 8/2000 | Berndtsson et al. | 73/864.87 |
| 6,106,778 A | * | 8/2000 | Oku et al. | 422/50 |
| 6,228,652 B1 | * | 5/2001 | Rodriguez et al. | 436/63 |
| 6,322,752 B1 | * | 11/2001 | Siddiqui et al. | 422/510 |
| 6,555,065 B1 | * | 4/2003 | Melet | 422/73 |
| 6,662,826 B1 | * | 12/2003 | Kokawa | 137/597 |
| 6,716,633 B2 | * | 4/2004 | Abo | 436/63 |
| 6,772,650 B2 | * | 8/2004 | Ohyama et al. | 73/864.24 |
| 6,812,032 B1 | * | 11/2004 | Carver et al. | 436/63 |
| 7,220,383 B2 | * | 5/2007 | Anderson et al. | 422/62 |
| 7,335,339 B2 | * | 2/2008 | Berndtsson | 422/549 |
| 2003/0070498 A1 | * | 4/2003 | Ohyama et al. | 73/863.01 |
| 2004/0105784 A1 | * | 6/2004 | Fukuju et al. | 422/68.1 |
| 2006/0210438 A1 | * | 9/2006 | Nagai et al. | 422/73 |
| 2008/0098828 A1 | * | 5/2008 | Li et al. | 73/863.73 |

\* cited by examiner

Fig. 8

| Measurement dialog | | | | | | | |
|---|---|---|---|---|---|---|---|

Sample number

ABC123456

OK

Cancel

Mode

○1 Ordinary measurement

○2 Small amount measurement

Measurement item

○1 CBC

○2 CBC NRBC

○3 CBC DIFF

○4 CBC DIFF RET

○5 CBC RET

○6 CBC DIFF NRBC

○7 CBC DIFF NRBC RET

MULTIPLE OPERATING MODE SAMPLE ANALYZER, ANALYZING METHOD, AND COMPUTER PROGRAM PRODUCT

RELATED APPLICATIONS

This application claims priority under 35 U.S.C. §119 to Japanese Patent Application No. JP2007-198681 filed Jul. 31, 2007, the entire content of which is hereby incorporated by reference.

FIELD OF THE INVENTION

The present invention relates to a sample analyzer, sample analyzing method, and computer program product.

BACKGROUND

Sample analyzers are used to measure components which are contained in biological samples such as urine or blood collected from a patient, and such analyzers are used daily in the field of clinical examinations in order to assist users to conduct diagnosis of illness and monitoring of medical treatment.

The amount of a sample required for analysis by the sample analyzer is stipulated beforehand in the sample analyzer, and this required amount or more must be collected from the patient.

In the case of infants, babies or children, and seriously ill patients, it may be difficult to collect the required amount of sample.

It is known that analysis can be performed using less than the ordinary amount of sample (hereinafter referred to as "small amount sample"). For example, Japanese Laid-Open Patent Publication No. 11-183472 discloses a method referred to as "capillary measurement" in which a user prepares a dilute sample of a small amount sample collected from a patient, and measures the dilute sample in the measurement section of a sample analyzer.

Disadvantages arise, however, in the capillary measurement disclosed in Japanese Laid-Open Patent Publication No. 11-183472 due to the labor involved in manually preparing the dilute sample, and the difficulty in obtaining adequate measurement accuracy which is affected by variations in the dilution operation.

SUMMARY

A first aspect of the present invention is a sample analyzer comprising: a sample preparation section for preparing a measurement sample from an undiluted biological sample and a reagent; a detector for detecting an analyte contained in the measurement sample prepared by the sample preparation section; and a controller in communication with the sample preparation section, the controller being configured to 1) control the sample preparation section so as to obtain a first amount of an undiluted biological sample from a first sample container, and prepare a first measurement sample of a first dilution ratio, when the undiluted biological sample in the first sample container is ordinary amount; and 2) control the sample preparation section so as to obtain a second amount of an undiluted biological sample from a second sample container, the second amount being less than the first amount, and prepare a second measurement sample of a second dilution ratio higher than the first dilution ratio, when the undiluted biological sample in the second sample container is small amount.

A second aspect of the present invention is a sample analyzing method in a sample analyzer being capable of analyzing a biological sample, comprising: a first step of obtaining a first amount of an undiluted biological sample from a first sample container, and preparing a first measurement sample of a first dilution ratio from the obtained undiluted biological sample and a reagent, when the undiluted biological sample in the first sample container is ordinary amount; a second step of obtaining a second amount of the undiluted biological sample from the second sample container, the second amount being less than the first amount, and preparing a second measurement sample of a second dilution ratio higher than the first dilution ratio from the obtained undiluted biological sample and the reagent, when the undiluted biological sample in the second sample container is small amount; and a third step of detecting an analyte contained in the measurement sample prepared in the first step or the second step.

A third aspect of the present invention is a computer program product for enabling a computer to execute a sample analyzing method in a sample analyzer which is capable of performing analysis of a biological sample, comprising: a computer readable medium; and software instructions, on the computer readable medium, for enabling the computer to perform predetermined operations comprising: a first step of obtaining a first amount of an undiluted biological sample from a first sample container, and preparing a first measurement sample of a first dilution ratio from the obtained undiluted biological sample and a reagent, when the undiluted biological sample in the first sample container is ordinary amount; a second step of obtaining a second amount of the undiluted biological sample from the second sample container, the second amount being less than the first amount, and preparing a second measurement sample of a second dilution ratio higher than the first dilution ratio from the obtained undiluted biological sample and the reagent, when the undiluted biological sample in the second sample container is small amount; and a third step of detecting an analyte contained in the measurement sample prepared in the first step or the second step.

BRIEF DESCRIPTION OF THE DRAWINGS

FIG. 8 shows an example of a measurement dialog;

DETAILED DESCRIPTION OF THE EMBODIMENT

The preferred embodiments of the present invention are described in detail hereinafter with reference to the accompanying drawings.

[Sample Analyzer Structure]

A sample analyzer S analyzes blood cell components (red blood cells (RBC), white blood cells (WBC), platelets (PLT), and hemoglobin (Hgb)) in blood samples collected from patients. The particles analyzed by the sample analyzer S are not particularly limited, and may be, in addition to blood cell components, biological particles such as cells contained in urine, body fluids (abdominal fluid, cerebral fluid, fluid of the thoracic cavity and the like), and biological particles which include platelet products.

Figure 4:
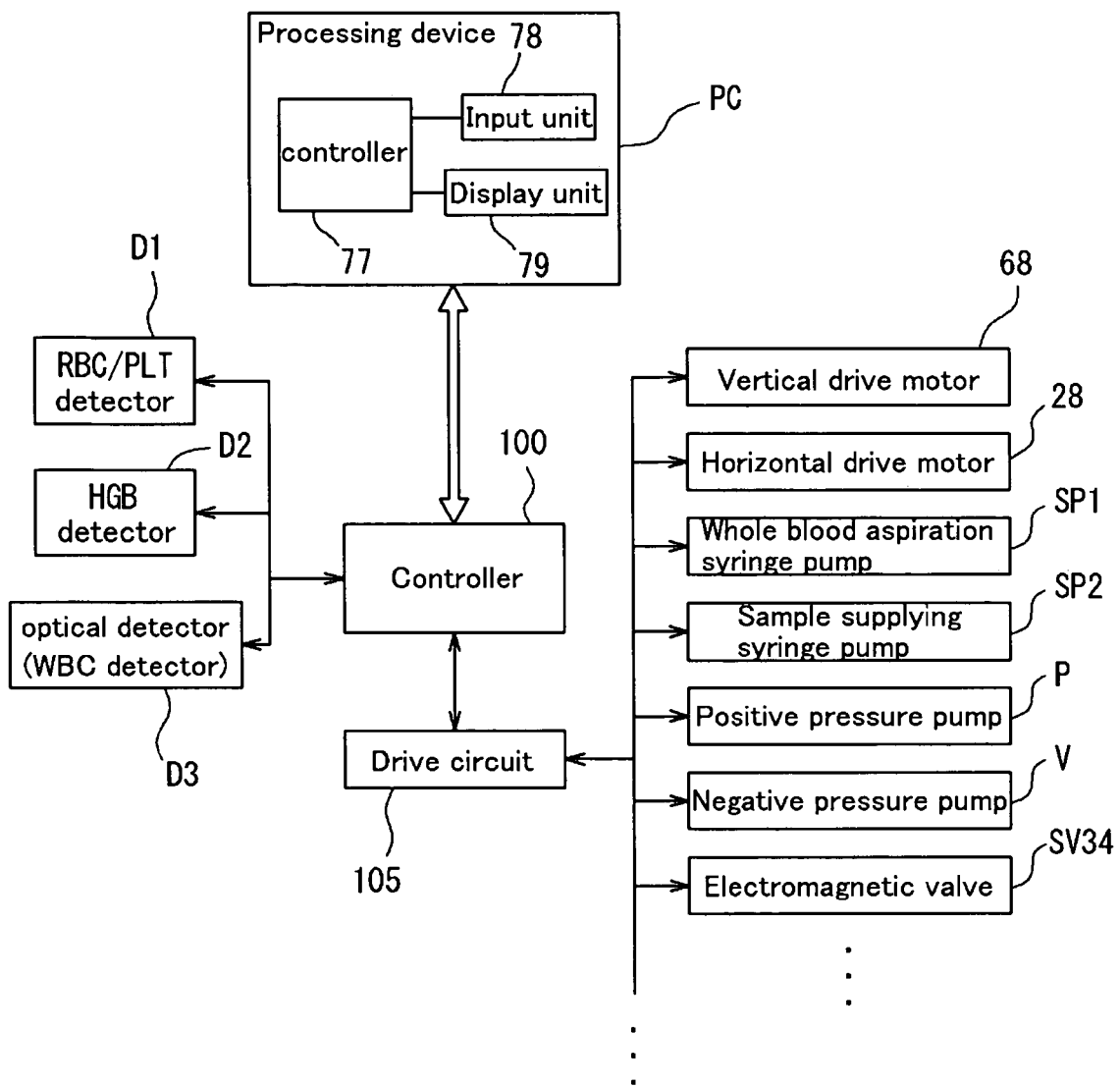
FIG. 4 is a control block diagram of the sample analyzer of FIG. 1.

The sample analyzer S is connected to a processing PC (typically, a personal computer on which the necessary computer programs are installed) which has a display, an input device, a CPU, a memory and the like, so that communication is enabled therebetween, and a sample analyzing system is configured by the sample analyzer S and the processing PC (refer to FIG. 4).

The processing PC has sample analysis software installed which performs the operations of the sample analyzer S, various settings related to analysis, display the analysis results and the like, and the processing PC is capable of issuing instructions to, and measurement data from, the sample analyzer S by communication.

The sample analyzer S is a device (blood analyzer) that measures a sample (blood) contained in a sample container 3, and is mainly configured by a device body 2, and a casing 1 that houses the device body 2.

The casing 1 is fabricated of synthetic resin and steel plate which has been processed to be rust-proof, and is fixedly attached to the device body 2 by an anchoring means such as bolts or the like. An opening 5 is formed in the lower right surface of the casing 1 (left side surface in FIG. 1), so that a sample container 3 can be inserted into the device body 2 through this opening 5. That is, a slider 7, which is provided with a mounting platform 6 near the end part of which a sample container 3 is mounted, is disposed at one end at the bottom of the device body 2 so as to be freely capable of ingress and egress from the opening 5. A freely rotatable cover 8, which is used to close the opening 5, is provided at the leading end of the slider 7, and this cover 8 is disposed so as to incline outward at a predetermined angle via a spring, which is not shown in the drawing (refer to FIG. 1). When the device is in a non-operating state (this state can be indicated on the outside of the device an unlighted lamp embedded in a button 15 provided on the side of the casing 1), the slider 7 is advanced outward from the device body 2 when a button 15 is pushed. Although the opening 5 is closed by the cover 8 is when the device in the non-operating state, the catch of a projection 8a of the cover 8 in a concavity 9 formed in the margin of the opening 5 is released when the slider 7 is advanced outside the device body 2, thus opening the cover 8. The cover 8 is inclined outward at a predetermined angle by the elastic force of the spring via the release of the catch of the projection 8a in the concavity 9.

A concavity (not shown in the drawing), into which the bottom part of a sample container 3 is inserted, if formed on the top surface of the mounting platform 6; when the bottom part of a sample container 3 is inserted into this concavity and the button 15 is pressed, the slider 7 is taken into the device body 2 and the container 3 is set at a predetermined position. The cover 8 is then raised against the elastic force of the spring and the cover 8 closes the opening 5. The cover 8 is prevented from opening because the projection 8a catches in the concavity 9. The sample analyzer S may be provided with a detection means such as a microswitch or the like to ensure the opening 5 is reliably closed by the cover 8 and enable the subsequent sample aspiration process.

Figure 1:
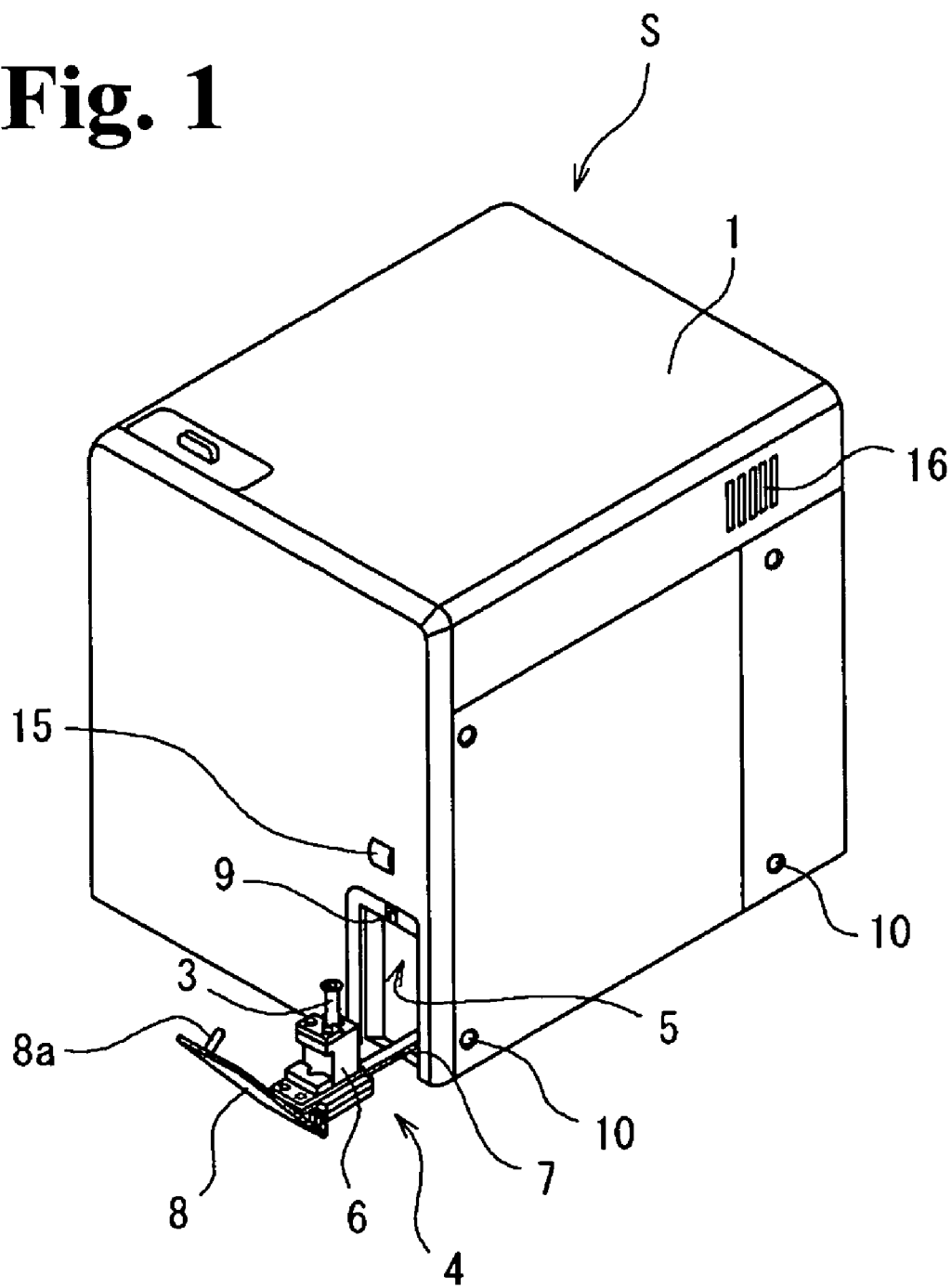
FIG. 1 is a general perspective view of a sample analyzer of an embodiment of the present invention.
Figure 2:
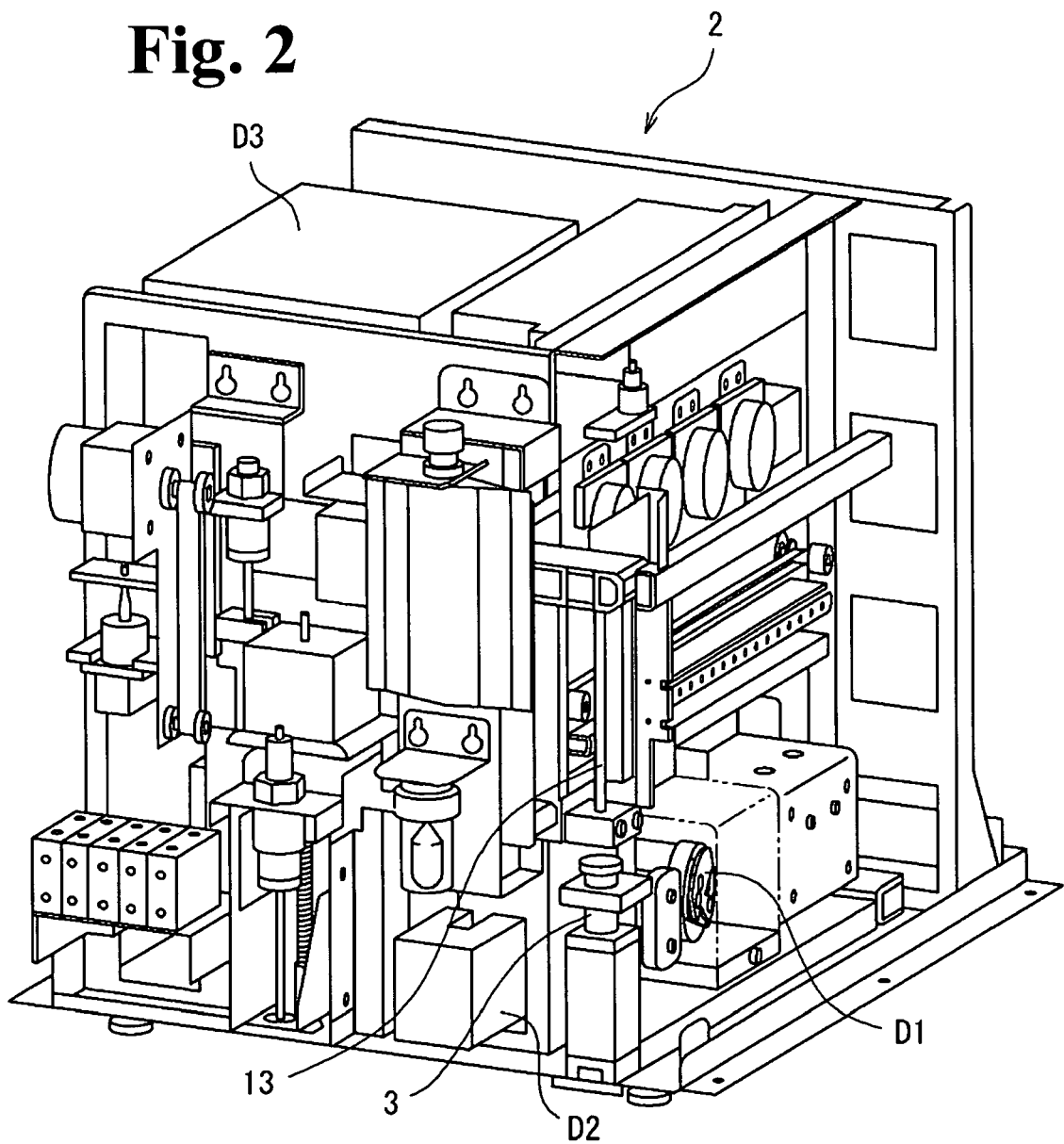
FIG. 2 is a perspective view showing the sample analyzer of FIG. 1 with the casing removed.
Figure 3:
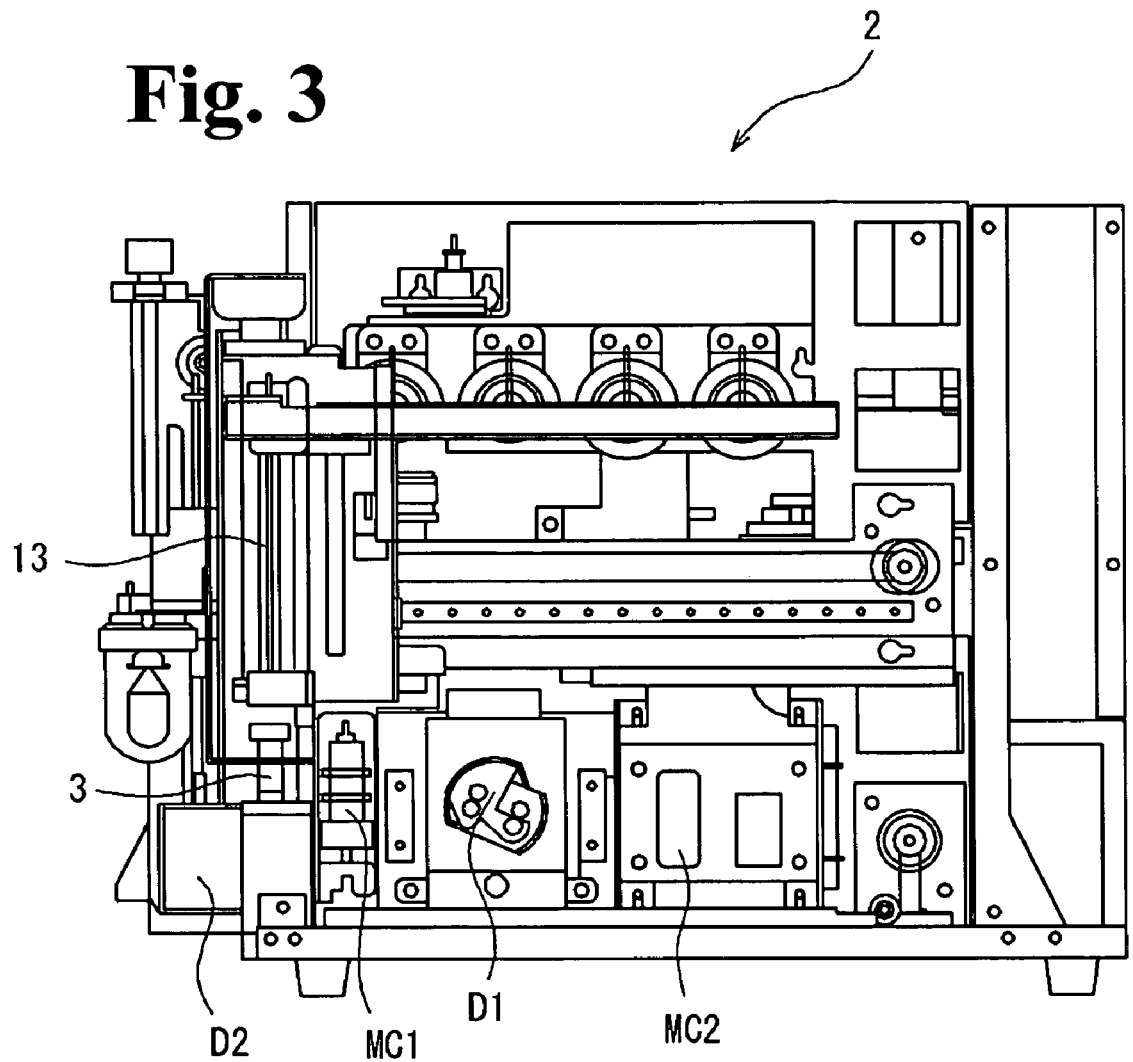
FIG. 3 is an illustration of the right side showing the sample analyzer of FIG. 1 with the casing removed.

A part of side surface of the casing 1 (right side surface in FIG. 1) is fixedly attached to the device body 2 by bolts or the like to allow easy maintenance and inspection within the device body 2. In FIG. 1, reference number 16 refers to an exhaust port which expels internally generated heat from the device body 2 via a fan (not shown in the drawing).

The sample analyzer S is provided with a sample placement area 4 in which to place a sample container 3 at a predetermined position within the device, and sample detectors D1, D2, and D3 which measure a measurement sample that has been prepared from a sample aspirated from a sample container 3 disposed in the sample placement area 4.

The sample analyzer S is also provided with an aspirating tube (pipette) 13, a first mixing chamber MC1, a second mixing chamber MC2, and, not shown in the drawing, a third mixing chamber MC3, fourth mixing chamber MC4, and fifth mixing chamber MC5. A sample, which has been aspirated from a sample container 3 disposed at the sample placement area 4 by the aspirating tube 13, is dispensed to the first through fifth mixing chambers MC1 through MC5, respectively. Measurement samples are respectively prepared using reagents (dilution liquid, staining solution, hemolytic agent) in the first through fifth mixing chambers MC1 through MC5. A measurement sample is prepared in the first mixing chamber MC1 to perform measurements related to red blood cells, hemoglobin, and platelets, and the prepared measurement sample is used in measurements performed by the detectors D1 and D2. A measurement sample is prepared to measure the number of white blood cells (WBC measurement sample) in the second mixing chamber MC2, a measurement sample is prepared to classify the white blood cells (DIFF measurement sample) in the third mixing chamber MC3, a measurement sample is prepared to measure nucleated red blood cells (NRBC measurement sample) in the fourth mixing chamber, and a measurement sample is prepared to measure reticulocytes (RET measurement sample) in the fifth mixing chamber MC5. The measurement samples prepared in the second through fifth mixing chambers MC2 through MC5 are used in measurement performed by the detector D3.

The detector D1 is configured as an RBC/PLT detector to perform an RBC measurement (measure the number of red blood cells) and a PLT measurement (measure the number of platelets). The RBC/PLT detector D1 is capable of performing the RBC and PLT measurements by a sheath flow DC detection method.

The detector D2 is configured as an HGB detector to perform an HGB measurement (measure the amount of hemoglobin in the blood). The detector D2 is capable of performing the HGB measurement by an SLS-hemoglobin method.

The detector D3 is configured as an optical detector capable of performing the WBC measurement (measure the number of white blood cells), DIFF measurement (classify white blood cells), NRBC measurement and RET measurement. The optical detector D3 performs the WBC measurement and the DIFF measurement and the like using a flow cytometric method that employs a semiconductor laser to detect, as characteristic parameters of the blood cells, the intensity of the forward scattered light, the intensity of the side scattered light, and the intensity of the side fluorescent light emitted from blood cells within a sheath flow irradiated by the laser light. The configuration of the detector D3 is described in detail later. The WBC measurement counts the number of white blood cells and calculates the concentration of the white blood cells in the sample; the DIFF measurement classifies the white blood cells into lymphocytes, basophiles, eosinophils, neutrophils, and monocytes, and calculates the concentration of each classification in the sample. The reticulocytes are measured in the RET measurement, and the nucleated red blood cells are measured in the NRBC measurement.

As shown in FIG. 4, the sample analyzer S is also provided with a controller 100 which controls the detectors D1, D2, and D3. The controller 100 has a CPU, memory and the like. The sample analyzer S is further configured by a drive circuit 105, a plurality of electromagnetic valves SV34 which open and close the flow paths used when delivering sample and reagent, a whole blood aspirating syringe SP1 to aspirate sample from a sample container 3 through an aspirating tube 13, a sample supplying syringe pump SP2 to supply the sample to the detectors, a vertical drive motor 68 to move the aspiration section 13 in vertical directions, a horizontal drive motor 28 to move the aspiration section 13 in horizontal directions, a positive pressure pump P, a negative pressure pump V and the like.

The controller 100 controls the various electromagnetic valves and motors via the drive circuit 105. The controller 100 is capable of communication with the processing device PC through a communication interface, which is not shown in the drawing, so as to exchange various signals and data with the processing device PC.

Figure 5:
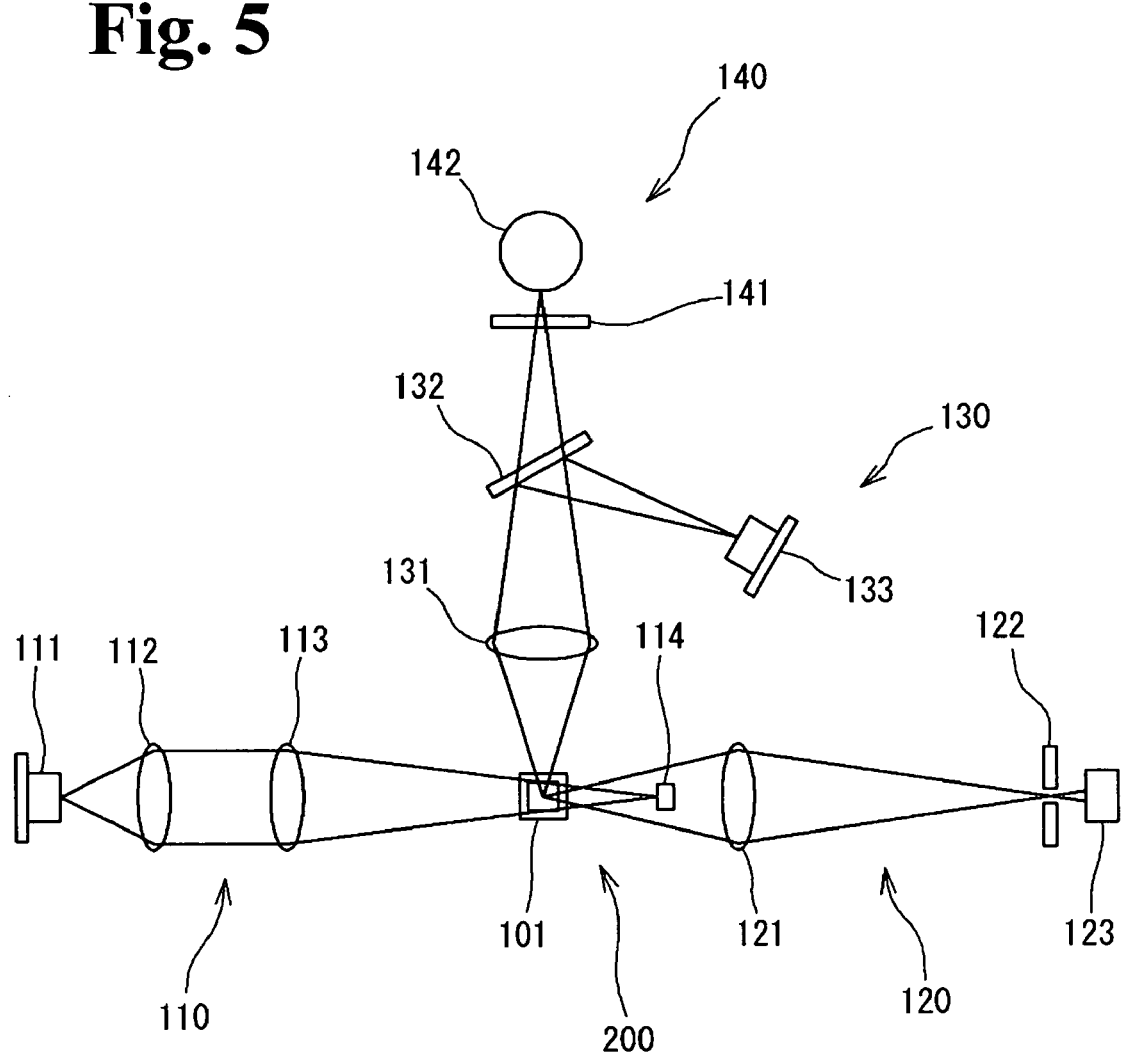
FIG. 5 is a brief structural view of a detector D3.

FIG. 5 briefly shows the structure of the previously mentioned detector D3. The detector D3 delivers a measurement sample into a flow cell 101 to generate a liquid flow within the flow cell 101, a semiconductor laser irradiates the blood cells contained in the liquid flow passing through the flow cell 101, and the detector D3 measures the light emitted by the blood cells; the detector D3 includes a sheath flow system 200, a beam spot forming system 110, a forward scattered light receiving system 120, a side scattered light receiving system 130, and a side fluorescent light receiving system 140.

A sheath flow system 200 creates a flow in which the measurement sample is encapsulated in sheath fluid within the flow cell 101 so that the blood cells are aligned in a row, thus improving the accuracy and the reproducibility of the blood cell count. The beam spot forming system 110 is configured to irradiate the light emitted from a semiconductor laser 111 on the flow cell 101 through a collimator lens 112 and a condenser lens 113. The beam spot forming system 110 is further provided with a beam stopper 114.

The forward scattered light receiving system 120 is configured to collect the light scattered in a forward direction via a forward collecting lens 121, and receive the light that has passed through a pinhole 122 at a photodiode (forward scattered light receiver) 123.

The side scattered light receiving system 130 is configured to collect the light scattered in a lateral direction via a side collecting lens 131, reflect a part of the light via a dichroic mirror 132, and receive the light at a photodiode (side scattered light receiver) 133.

Light scattering is a phenomenon that occurs when the direction in which light is traveling is changed by the presence of particles such as blood cells and the like which act as obstacles to the light in the direction of travel. Information relating to the size and quality of the particle can be obtained by detecting the scattered light. Information relating to the size of the particle (blood cell) is particularly obtainable from the forward scattered light. Information about the interior of the particle is also obtainable from the side scattered light. When a blood cell particle is irradiated by laser light, the intensity of the side scattered light is dependent on the complexity of the cell interior (shape, size, and density of the nucleus as well as the amount of granularity). The measurement to classify the white blood cells as well as other measurements can therefore be performed using the characteristics of the side scattered light intensity.

The side fluorescent light receiving system 140 is configured so that the light which passes through the dichroic mirror 132 is directed through a spectral filter 141 and be received by a photomultiplier (fluorescent light receiver) 142.

When light irradiates a fluorescent substance such as a stained blood cell, light is emitted that has a longer wavelength than the wavelength of the irradiating light. The intensity of the fluorescent light is enhanced by the stain, and information relating to the degree of staining of the blood cell is obtainable by measuring this fluorescent intensity. The classification of the while blood cells and other measurements can therefore be accomplished by detecting the difference in the (side) fluorescent light intensity.

Figure 6:
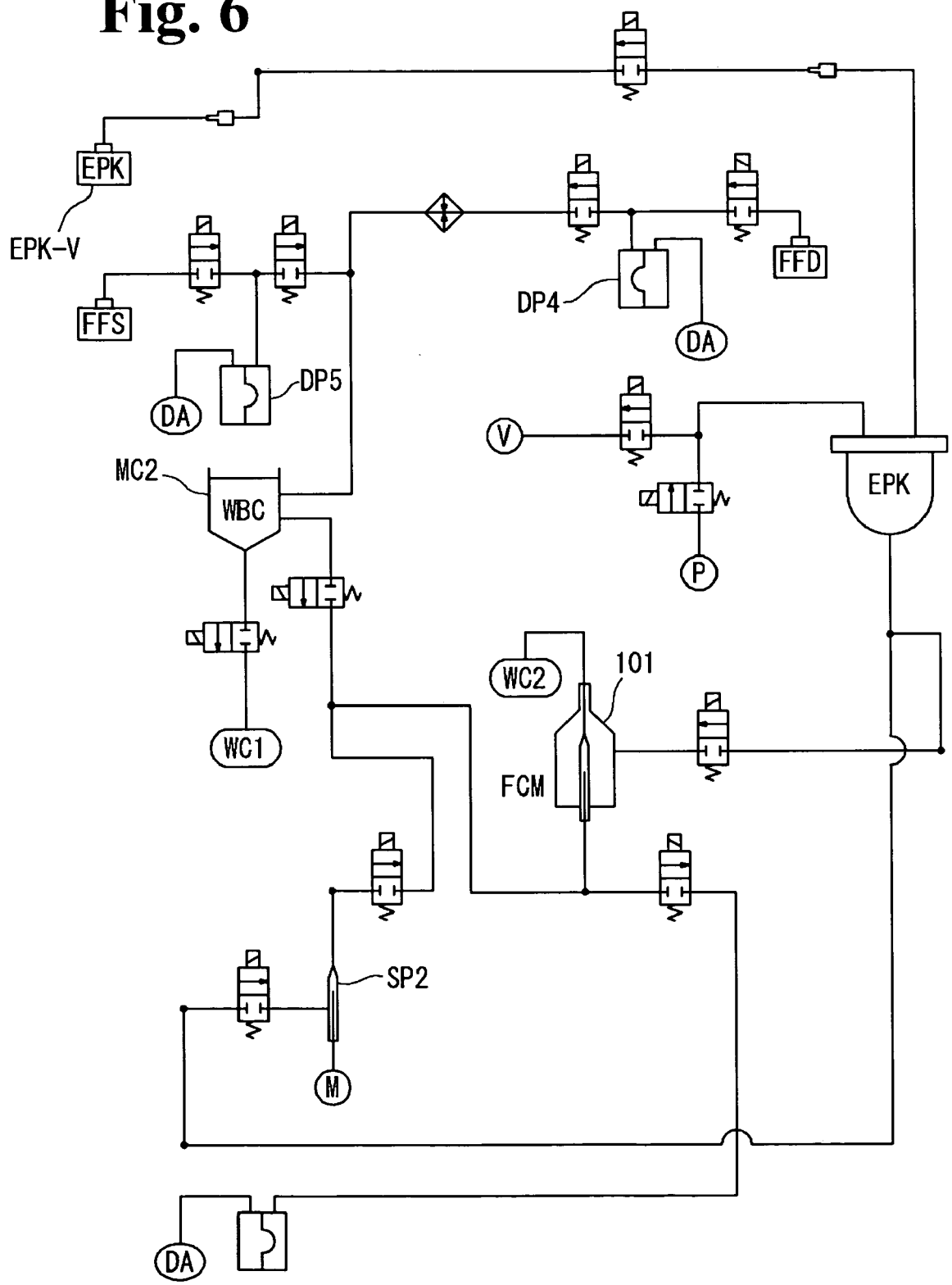
FIG. 6 is a fluid circuit diagram showing a part of the fluid circuit of a WBC measurement system.

FIG. 6 is fluid circuit diagram showing a part of the fluid circuit of the WBC measuring system used to prepare the measurement sample in the second mixing chamber MC2, and to perform the WBC measurement (measuring the number of white blood cells) by the detector D3. In FIG. 6, the mixing chamber MC1, the third through fifth mixing chambers MC3 through 5, and the fluid circuit connected to these chambers are omitted from the drawing to facilitate understanding.

As shown in FIG. 6, the fluid circuit of the WBC measuring system includes the second mixing chamber MC2, the flow cell 101 which is part of the detector D3, a diaphragm pump DP4 to supply a hemolytic agent FFD to the second mixing chamber MC2, a diaphragm pump DP5 to supply a staining solution FFS to the second mixing chamber MC2, a syringe pump SP2 to supply the measurement sample to the flow cell 101, and a dilution liquid container EPK-V to accommodate a dilution liquid (washing liquid) EPK to wash the flow cell 101 and the like.

[Sample Measurement Flow]

Figure 7:
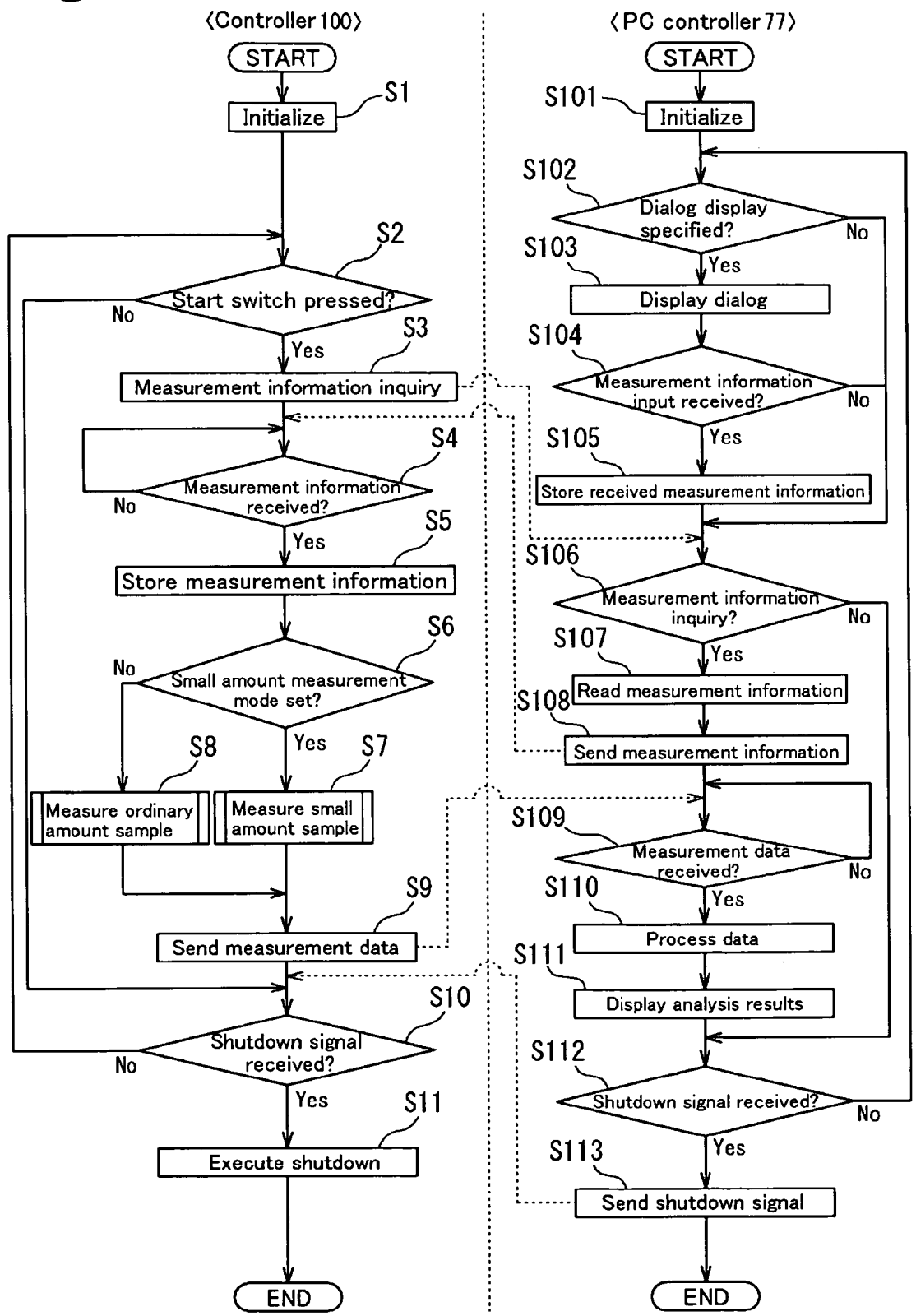
FIG. 7 shows an example of the general flow of the analysis process performed by the sample analyzer.

An example of the complete flow of the analysis process performed by the sample analyzer S is shown in FIG. 7. The process described below is controlled by the processing device PC, and more specifically by a controller 77 of the processing device PC, and the controller 100 of the device body 2.

When the power source of the device body 2 is first turned ON, the controller 100 is initialized (step S1). In this initialization operation, program initialization is performed and the drive units of the device body 2 are returned to their origin positions.

In step S2, the controller 100 determines whether or not a user has pressed the start switch. The process advances to step S3 when the controller 100 determines that the start switch has been pressed (YES), whereas the process advances to step S10 when the controller 100 determines the start switch has not been pressed (NO).

In step S3 the controller 100 sends a signal inquiring for measurement information to the controller 77 of the processing device PC.

When the power source of the processing device PC is turned ON, the controller 77 of the processing device PC is initialized (step S101). In this initialization operation, program initialization and the like is performed. When initialization is completed, a display unit 79 displays a menu screen (not shown in the drawing), which includes a measurement dialog display button to specify a measurement dialog display in order to select the mode and measurement items. The user can operate an input unit 78 to select a measurement dialog display button to specify the measurement dialog display of the menu screen.

In step S102 the controller 77 determines whether or not the measurement dialog display has been specified (whether or not the measurement dialog display button has been selected to specify the measurement dialog display of the menu screen). The process advances to step S103 when the controller 77 has determined that the measurement dialog display has been specified (YES), whereas the process moves to step S106 when the controller 77 has determined that the measurement dialog display has not been specified (NO).

In step S103 the controller 77 displays the measurement dialog shown in FIG. 8 on the display unit 79. The user may operate the input unit 78 to input a sample number, and select a measurement mode (ordinary measurement and small amount measurement) and a measurement item.

In step S104 the controller 77 determines whether or not measurement information that includes information of the sample number, measurement mode, and measurement item has been received. The process continues to step S107 when the controller 77 has determined that measurement information has been received (YES), whereas the process moves to step S106 when the controller 77 has determined that measurement information has not been received (NO).

In step S105 the controller 77 stores the input measurement information.

In step S106 the controller 77 determines whether or not a measurement information inquiry signal has been received from the controller 100 of the processing device 2. The process moves to step S107 when the controller 77 has determined that a measurement information inquiry signal has been received from the controller 100 of the device body 2, whereas the process moves to step S112 when the controller 77 has determined that a measurement information inquiry signal has not been received from the controller 100 of the processing device 2.

In step S107 the controller 77 reads the measurement information stored in the storage unit of the controller 77. The measurement information includes the type of measurement mode desired by the user, that is, a measurement mode that uses a normal amount sample, or a measurement mode that uses a small amount sample. The measurement items are also included. In the present embodiment, measurement items may be selected from among seven menu types, as shown in FIG. 8. In the present embodiment, CBC is a compulsory measurement item and the menus suitably combine CBC and DIFF, NRBC, and RET, however, the present invention is not limited to this arrangement inasmuch as CBC may be combined with desired measurement items as necessary. When user input measurement information has not been received in step S104, then the measurement information input during the previous sample measurement (or default measurement information when measurement information has never once been input up to the previous sample measurement) is read from the storage unit of the controller 77. In this case, the sample number is automatically set according to a predetermined rule. The CBC item alone is set automatically as the measurement item when the small amount measurement mode has been received as the measurement mode, and not any measurement item selection has been received.

In step S108 the controller 77 sends the read measurement information to the controller 100 of the device body 2.

The controller 100 of the device body 2 determines whether or not measurement information has been received from the controller 77 in step S4. The process continues to step S5 when the controller 100 has determined that the measurement information has been received (YES), whereas the process returns to the same step S4 when measurement information has not been received. The controller 100 stores the received measurement information in a storage unit of the controller 100.

In step S106 the controller 100 determines whether or not the small amount measurement mode is set by the received measurement information. The process moves to step S7 when the controller 100 determines that the small amount measurement mode is set (YES), whereas the process moves to step S8 and the ordinary amount sample measurement is executed when the controller 100 determines that the small amount measurement mode is not set. Details of the small amount sample measurement (step S7) and the ordinary amount sample measurement (step S8) are described later.

The controller 100 sends the data obtained by the measurement to the controller 77 of the processing PC in step S9. The controller 77 of the processing PC determines whether or not measurement data have been received from the controller 100 of the device body 2 in step S109. The process advances to step S110 when the controller 77 determines that measurement data have been received (YES), and the received measurement data are processed and in step S111 the analysis results are displayed and the distribution maps are suitably displayed on the display unit 79. When the controller 77 determines that measurement data have not been received (NO), the process returns to step S109. The same data processing is performed in the measurement data processing of step S110 whether the ordinary measurement mode or the small amount measurement mode has been set. Although a measurement sample with a higher dilution ratio is measured in the small amount measurement mode than in the ordinary measurement mode, a greater amount of measurement sample can be measured than in the ordinary measurement mode by measuring measurement samples for a longer time than the measurement time in the ordinary measurement mode. Therefore, the small amount sample can be more precisely analyzed without performing different data processing in the small amount measurement mode than the processing of the measurement data in the ordinary measurement mode.

In step S112 the controller 77 determines whether or not a shutdown signal has been received. The process continues to step S113 when the controller 77 has determined that a shutdown signal has been received (YES), whereas the process returns to step S102 when the controller 77 has determined that a shutdown signal has not been received (NO). In step S113 the controller 77 sends a shutdown signal to the controller 100 and the processing ends on the processing device PC side.

In step S110 the controller 100 determines whether or not a shutdown signal has been received from the controller 77 of the processing device PC. The process continues to step S11 when the controller 100 has determined that a shutdown signal has been received (YES), whereas the process returns to step S2 when the controller 100 has determined that a shutdown signal has not been received (NO). In step S11 the controller 100 shuts down the device body 2 and the process ends.

[Ordinary Mode]

Figure 9:
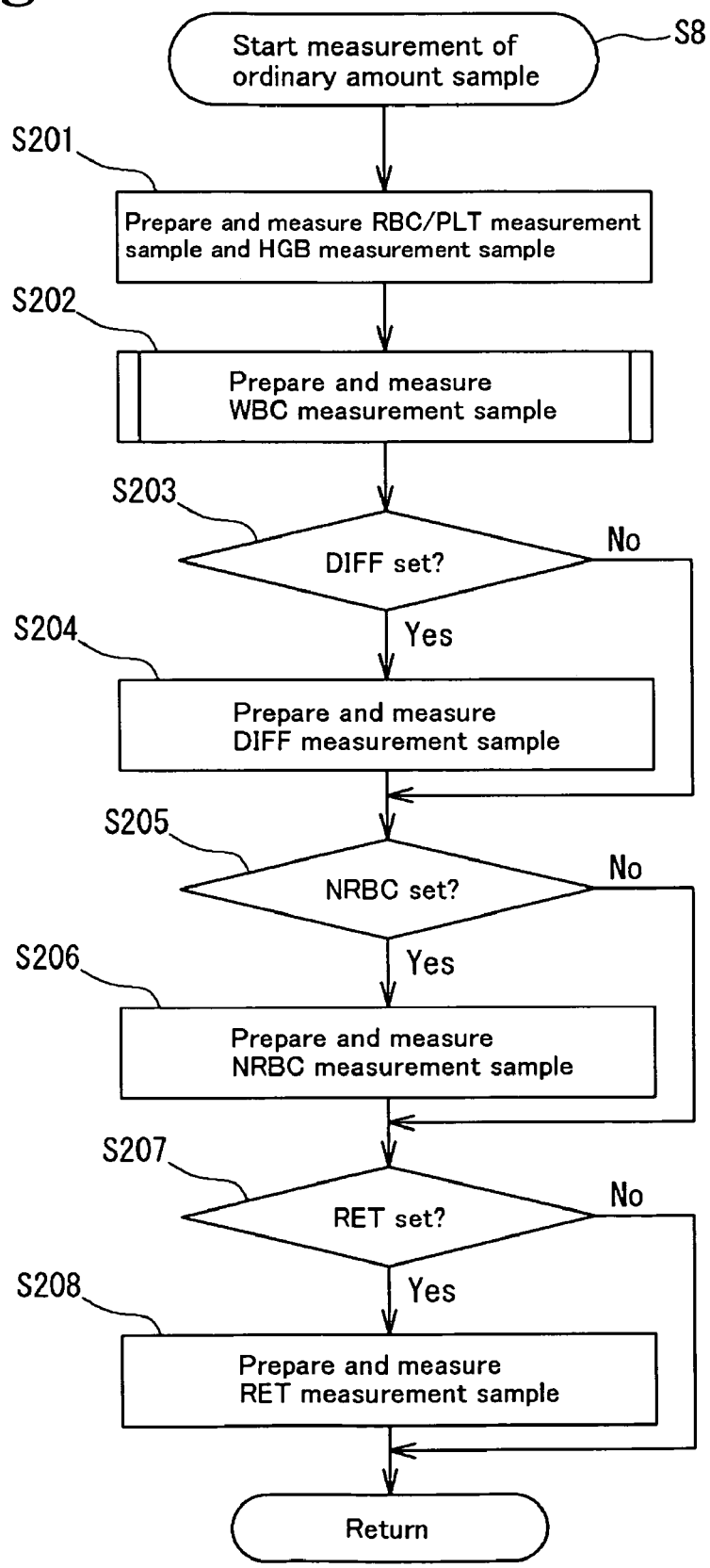
FIG. 9 is a flowchart showing the ordinary measurement mode.

The ordinary mode in which an ordinary amount sample is measured in step S8 is described below referring to FIG. 9.

A predetermined amount of sample (for example, 75 μL; the numeric values in the parentheses below are examples of the amounts used and the amounts aspirated of the sample and reagent) is first aspirated by a syringe pump through an aspirating tube.

In step S201 the controller 100 prepares and measures an RBC/PLT measurement sample and an HGB measurement sample. Specifically, a part (4 µL) of a sample is dispensed from the aspirating tube into the first mixing chamber MC1, and predetermined amount (2.0 mL) of dilution liquid is mixed therewith to prepare a measurement sample (2.0 ml) which has been diluted 501 fold. Part of the prepared measurement sample (1.0 mL of the RBC/PLT measurement sample) is introduced to the RBC/PLT detector D1 (electrical resistance type sensor), and particle detection and data collection are performed for 10.5 seconds. The amount of the measured RBC/PLT measurement sample is 10.3 µl. The remaining measurement sample (1.0 ml) is introduced to the HGB detector D2, and a predetermined amount (0.5 mL) of hemolytic agent is mixed therewith to prepare an HGB measurement sample (1.5 mL) which has been diluted 751 fold. The hemoglobin concentration is measured based on the HGB measurement sample.

In step S202 the controller 100 prepares and measures a WBC measurement sample. Details of the preparation and measurement of the WBC measurement sample are described later.

In step S203 the controller 100 determines whether or not DIFF is set as a measurement item. The process advances to step S204 when the controller 100 determines that DIFF is set as a measurement item (YES), whereas the process advances to step S205 when the controller 100 determines that DIFF is not set as a measurement item (NO).

In step S204 the controller 100 prepares and measures a DIFF measurement sample.

In step S205 the controller 100 determines whether or not NRBC is set as a measurement item. The process moves to step S206 when the controller 100 determines that NRBC is set as a measurement item (YES), whereas the process advances to step S207 when the controller 100 determines that NRBC is not set as a measurement item (NO).

In step S206 the controller 100 prepares and measures an NRBC measurement sample.

In step S207 the controller 100 determines whether or not RET is set as a measurement item. The process continues to step S208 when the controller determines that RET is set as a measurement item (YES), whereas the process advances to step S209 when the controller 100 determines that RET is not set as a measurement item (NO).

In step S208 the controller 100 prepares and measures an RET measurement sample. Specifically, a part (5 µL) of a sample is dispensed from the aspirating tube into the fifth mixing chamber MC5, and a predetermined amount (1.0 ml) of dilution liquid and a predetermined amount (20 µL) of staining solution are mixed therewith to prepare an RET measurement sample (1.0 ml) which is diluted 205 fold. The diluted measurement sample (1.0 mL) is introduced to the WBC detector D3 (optical detector), and particle detection and data collection are performed for 3.2 seconds. The amount of the measured RET measurement sample is 2.99 µL).

[WBC Measurement]

Figure 10:
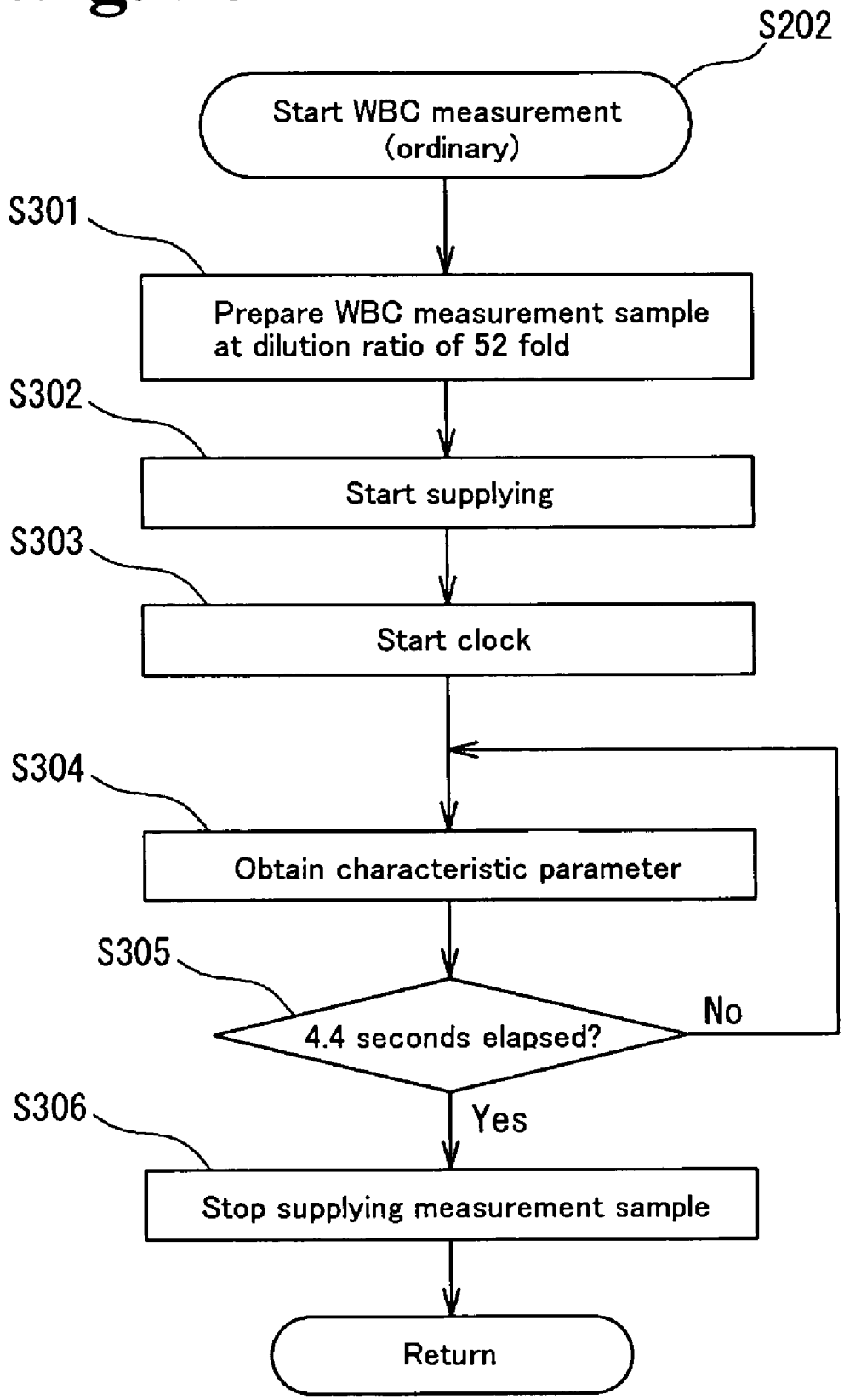
FIG. 10 is a flowchart showing the WBC measurement in the ordinary measurement mode.

FIG. 10 shows the flow of the WBC measurement (ordinary) in step S202.

In step S301 the controller 100 prepares a WBC measurement sample which has a dilution ratio of 52 fold. Specifically, a part (20 µL) of a sample is dispensed from the aspirating tube into the second mixing chamber MC2, and a predetermined amount (1.0 mL) of a hemolytic agent and a predetermined amount (20 µL) of a staining solution are mixed therewith to prepare a WBC measurement sample (1.0 µL) which is diluted 52 fold.

In step S302 the prepared WBC measurement sample begins to be supplied to the WBC detector D3.

In step S303 a clock is started to measure the time from when the measurement sample begins to be supplied, and in step S304 the characteristics parameters of the measurement sample are obtained by the WBC detector D3.

In step S305 the controller 100 determines whether or not 4.4 seconds has elapsed since the clock was started; the process returns to step S304 when the controller 100 determines that 4.4 seconds has not elapsed since the clock started (NO), whereas the process continues to step S306 when the controller 100 determines that 4.4 seconds has elapsed since the clock started (YES), and in step S306 the controller 100 stops supplying the WBC measurement sample to the WBC detector D3. The amount of the WBC sample measured in the WBC measurement is 39.8 µL.

In the DIFF measurement of step S204 and the NRBC measurement of step S206, each measurement sample is prepared using the same amount of sample as in the previously described WBC measurement, and diluted 52 fold using the hemolytic agent and staining solution of each measurement, and the characteristic parameters of the blood cell particles within each measurement sample are obtained by the WBC detector D3 in the same process sequence as in the WBC measurement.

[Small Amount Mode]

Figure 11:
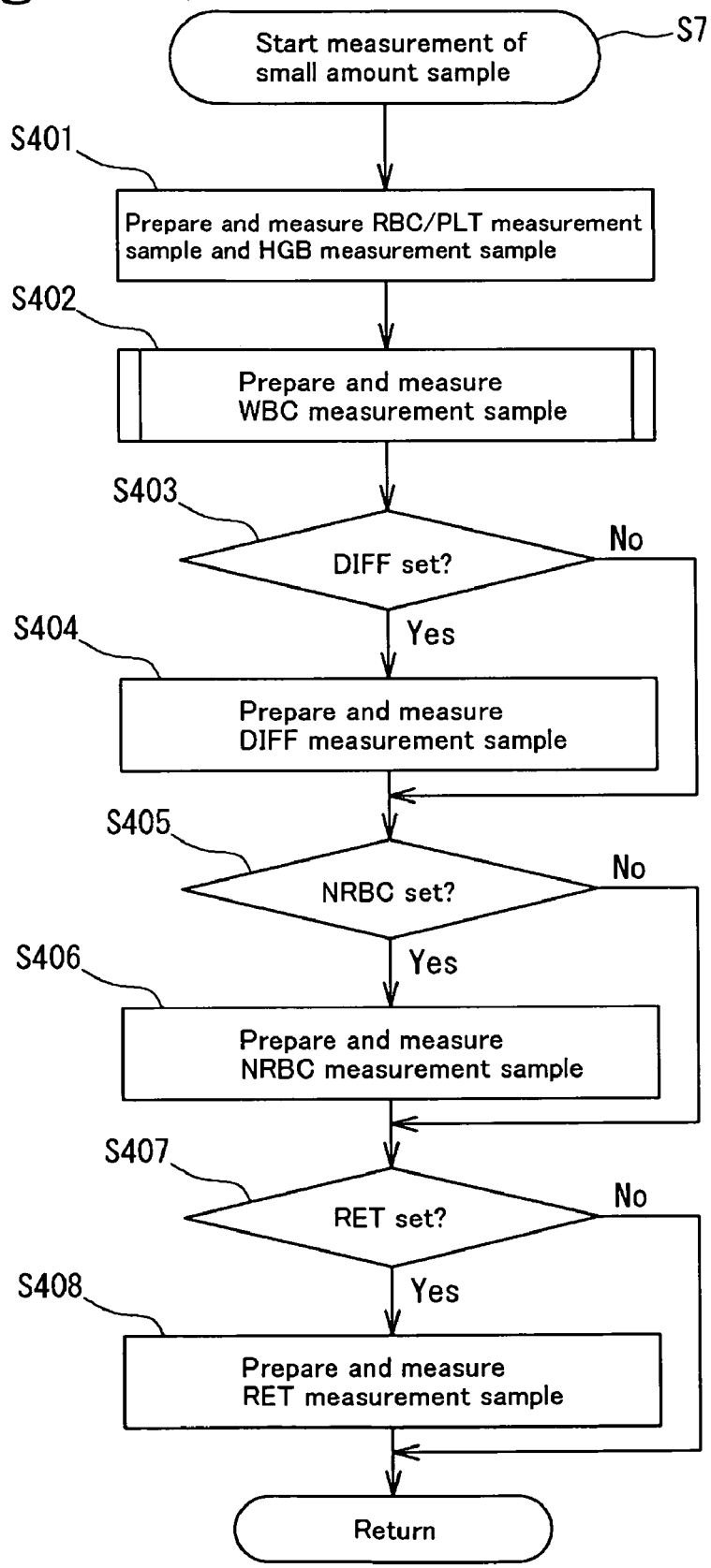
FIG. 11 is a flowchart showing the small amount measurement mode.

The small amount measurement mode in which a small amount of sample is measured in step S7 is described below referencing FIG. 11.

A predetermined amount of sample (48 µL) is first aspirated through the aspirating tube by a syringe pump.

In step S401 the controller 100 prepares and measures an RBC/PLT measurement sample and an HGB measurement sample. Specifically, a part (4 µL) of a sample is dispensed from the aspirating tube into the first mixing chamber MC1, and predetermined amount (2.0 mL) of dilution liquid is mixed therewith to prepare a measurement sample (2.0 mL) which has been diluted 501 fold. Part of the prepared measurement sample (1.0 mL of the RBC/PLT measurement sample) is introduced to the RBC/PLT detector D1 (electrical resistance type sensor), and particle detection and data collection are performed for 10.5 seconds. The amount of the measured RBC/PLT measurement sample is 10.3 µL. The remaining measurement sample (1.0 mL) is introduced to the HGB detector D2, and a predetermined amount (0.5 mL) of hemolytic agent is mixed therewith to prepare an HGB measurement sample (1.5 mL) which has been diluted 751 fold. The hemoglobin concentration is measured based on the HGB measurement sample.

In step S402 the controller 100 prepares and measures a WBC measurement sample. Details of the preparation and measurement of the WBC measurement sample are described later.

In step S403 the controller 100 determines whether or not DIFF is set as a measurement item. The process advances to step S404 when the controller 100 determines that DIFF is set as a measurement item (YES), whereas the process moves to step S405 when the controller 100 determines that DIFF is not set as a measurement item (NO).

In step S404 the controller 100 prepares and measures a DIFF measurement sample.

In step S405 the controller 100 determines whether or not NRBC is set as a measurement item. The process moves to step S406 when the controller 100 determines that NRBC is set as a measurement item (YES), whereas the process advances to step S407 when the controller 100 determines that NRBC is not set as a measurement item (NO).

In step S406 the controller 100 prepares and measures an NRBC measurement sample.

In step S407 the controller 100 determines whether or not RET is set as a measurement item. The process continues to step S408 when the controller determines that RET is set as a measurement item (YES), whereas the process moves to step S9 when the controller 100 determines that RET is not set as a measurement item (NO).

In step S408 the controller 100 prepares and measures an RET measurement sample. Specifically, a part (5 µL) of a sample is dispensed from the aspirating tube into the fifth mixing chamber MC5, and a predetermined amount (1.0 mL) of dilution liquid and a predetermined amount (20 µL) of staining solution are mixed therewith to prepare an RET measurement sample (1.0 mL) which is diluted 205 fold. The diluted measurement sample (1.0 mL) is introduced to the WBC detector D3 (optical detector), and particle detection and data collection are performed for 3.2 seconds. The amount of the measured RET measurement sample is 2.99 µL.

[WBC Measurement]

Figure 12:
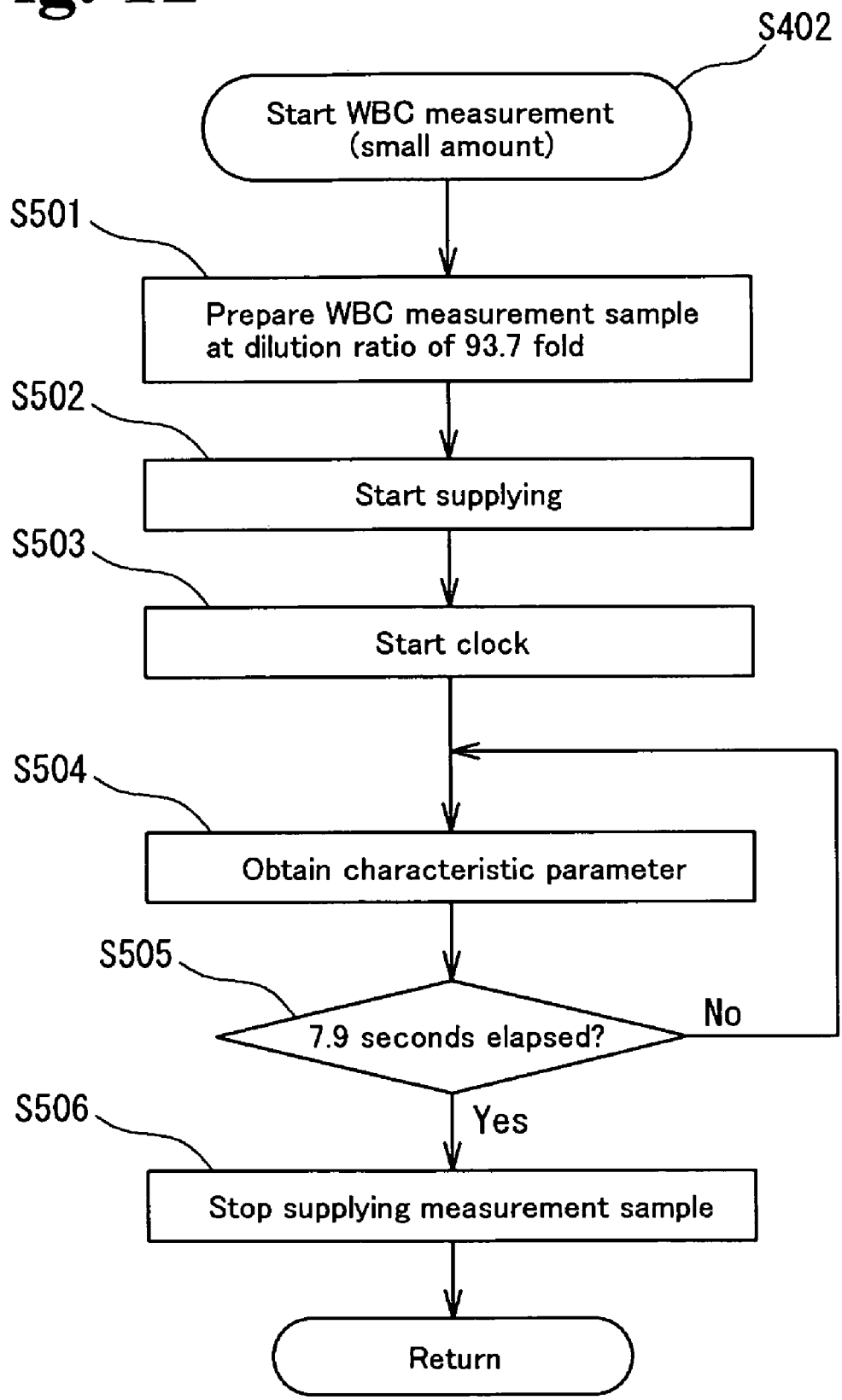
FIG. 12 is a flowchart showing the WBC measurement in the small amount measurement mode.

FIG. 12 shows the flow of the WBC measurement (small amount) in step S402.

In step S501 the controller 100 prepares a WBC measurement sample which has a dilution ratio of 93.7 fold. Specifically, a part (11 µL) of the sample is dispensed from the aspirating tube into the second mixing chamber MC2, and a predetermined amount (1.0 mL) of hemolytic agent and a predetermined amount (20 µL) of staining solution are mixed therewith to prepare a WBC measurement sample (1.0 mL) which has been diluted 93.7 fold.

In step S502 the prepared WBC measurement sample begins to be supplied to the WBC detector D3.

In step S503 a clock is started to measure the time from when the measurement sample begins to be supplied, and in step S504 the characteristic parameters of the measurement sample are obtained by the WBC detector D3.

In step S505 the controller 100 determines whether or not 7.9 seconds has elapsed since the clock was started; the process returns to step S504 when the controller 100 determines that 7.9 seconds has not elapsed since the clock started (NO), whereas the process continues to step S506 when the controller 100 determines that 7.9 seconds has elapsed since the clock started (YES), and in step S506 the controller 100 stops supplying the WBC measurement sample to the WBC detector D3. The amount of the WBC sample measured in the WBC measurement is 71.4 µL.

In the DIFF measurement of step S404 and the NRBC measurement of step S406, each measurement sample is prepared using the same amount of sample as in the previously described WBC measurement, and diluted 93.7 fold using the hemolytic agent and staining solution of each measurement, and the characteristic parameters of the blood cell particles within each measurement sample are obtained by the WBC detector D3 in the same process sequence as in the WBC measurement.

The sample analyzer S is configured so that the measurement sample supplying speed at which the measurement sample is supplied to the detector in the small amount measurement mode is identical to the measurement sample supplying speed at which the measurement sample is supplied to the detector in the previously described ordinary measurement mode.

In the sample analysis method of the embodiment as described above, the preparation of measurement sample is automated even when measuring a small amount sample. Labor is therefore eliminated and variations in the dilution ratio are avoided. Thus, measurement precision is improved.

In the sample analysis method of the present embodiment, a lesser amount of sample (48 µL) is aspirated when the small amount measurement mode is selected compared to the amount of sample (75 µL) when the ordinary measurement mode is selected. Although the dilution ratio of the measurement sample is, for example, high (93.7 fold) in the case of the WBC measurement compared to the ordinary measurement mode (52 fold), the measurement time is longer (7.9 seconds) for measuring the sample than the measurement time (4.4 seconds) in the ordinary measurement mode and a larger amount of measurement sample (71.4 µL) is measured than the measurement amount (39.8 µL) in the ordinary measurement mode so that measurement precision is increased even with the higher dilution.

In the present embodiment, when, for example, WBC measurement is performed when the small amount measurement mode is selected, the measurement sample is measured for a longer time than in the ordinary measurement mode, so that a larger amount of measurement sample can be measured than in the ordinary measurement mode even though the speed of the measurement sample flowing to the detector in the small amount measurement mode is identical to the speed of the measurement sample flowing to the detector in the ordinary measurement mode. Therefore, the speed at which the measurement sample is supplied to the detector can be identical for any measurement mode, and the measurement of the samples can be performed under identical conditions. Moreover, the structure of the apparatus can also be simplified.

In the present embodiment, the amount of reagent used in the preparation of each measurement sample in the ordinary measurement mode is identical to the amount of reagent used in the preparation of each measurement sample in the small amount measurement mode. The structure of the apparatus can therefore be simplified.

If a larger amount of measurement sample is used in the ordinary measurement mode than in the small amount measurement mode, the measurement time need not be longer in the small amount measurement mode than in the ordinary measurement mode. In this case, the measurement of a large amount of measurement sample increases measurement precision even though the dilution ratio is high.

The aspiration amount, dilution ratio, and measurement time of the sample in the previously described embodiment are merely simple examples and can be variously modified in accordance with the measurement sample.

Although the sample analyzer S and the processing device PC are separate in the present embodiment, the sample analyzer and the processing device may be integrated in a single unit.

Although the setting of the measurement mode (ordinary measurement and small amount measurement) is performed in the processing device PC in the present embodiment, the sample analyzer S may be configured to perform the setting of the measurement mode in the sample analyzer S.

Although same data processing is performed when either the ordinary measurement mode or the small amount measurement mode is set in the processing of the measurement data in step S110 in the present embodiment, a calculation process may also be performed on the measurement data obtained form the device body 2 in accordance with the difference in the dilution ratio of the measurement sample in the ordinary measurement mode and the dilution ratio of the measurement sample in the small amount measurement mode when the small amount measurement mode is set.

What is claimed is:

1. A blood analyzer comprising:
a sample preparation section for preparing a measurement sample from an undiluted blood in a sample container and a reagent;
a detector comprising a flow cell for passing the measurement sample prepared by the sample preparation section and detecting blood components contained in the measurement sample passing through the flow cell;
a process control system having a command mode input configured to specify a first operating mode or a second operating mode; and
a controller in communication with the sample preparation section and configured to carry out the first operating mode or the second operating mode, where
1) in the first operating mode, the controller controls the sample preparation section so as to obtain a first amount of the undiluted blood from the sample container, and prepare a first measurement sample of a first dilution ratio, and the detector detects blood components contained in a first amount of the first measurement sample; and
2) in the second operating mode, the controller controls the sample preparation section so as to obtain a second amount of the undiluted blood from a sample container, the second amount of the undiluted blood being less than the first amount of the undiluted sample, and prepare a second measurement sample of a second dilution ratio higher than the first dilution ratio, and the detector detects blood components contained in a second amount of the second measurement sample larger than the first amount of the first measurement sample.

2. The blood analyzer of claim 1, further comprising
a sample supplier for supplying the measurement sample prepared by the sample preparation section to the flow cell, wherein
1) in the first operating mode, the controller controls the sample supplier so as to supply the first measurement sample to the flow cell for a first period; and
2) in the second operating mode, the controller controls the sample supplier so as to supply the second measurement sample to the flow cell for a second period longer than the first period.

3. The blood analyzer of claim 2, wherein the controller is configured to control the sample supplier so as to supply the measurement samples prepared by the sample preparation section to the flow cell at a predetermined speed, regardless of whether in the first operating mode or the second operating mode.

4. The blood analyzer of claim 1, further comprising a sample supplier for supplying the measurement sample prepared by the sample preparation section to the flow cell, wherein
1) in the first operating mode, the controller controls the sample supplier so as to supply the first amount of the first measurement sample to the flow cell; and
2) in the second operating mode, the controller controls the sample supplier so as to supply the second amount of the second measurement sample to the flow cell.

5. The blood analyzer of claim 1, wherein the detector comprises:
a light emitting section for irradiating light on the measurement sample passing through the flow cell; and
a light receiving section for receiving light from the measurement sample irradiated by the light emitting section.

6. The blood analyzer of claim 1, wherein the controller is configured to control the sample preparation section so as to prepare the measurement sample using substantially a similar amount of the reagent, regardless of whether in the first operating mode or in the second operating mode.

7. A method of analyzing blood in a sample analyzing, the method comprising:
providing a sample preparation section for preparing a measurement sample from an undiluted blood in a sample container and a reagent;
providing a detector comprising a flow cell for passing the measurement sample prepared by the sample preparation section and detecting blood components contained in the measurement sample passing through the flow cell;
providing a process control system having a command mode input configured to specify a first operating mode or a second operating mode; and providing a controller in communication with the sample preparation section and operating the analyzer to carry out the first operating mode or the second operating mode, where
1) in the first operating mode, the controller controls the sample preparation section so as to obtain a first amount of the undiluted blood from the sample container, and prepare a first measurement sample of a first dilution ratio, and the detector detects blood components contained in a first amount of the first measurement sample; and
2) in the second operating mode, the controller controls the sample preparation section so as to obtain a second amount of the undiluted blood from a sample container, the second amount of the undiluted blood being less than the first amount of the undiluted sample, and prepare a second measurement sample of a second dilution ratio higher than the first dilution ratio, and the detector detects blood components contained in a second amount of the second measurement sample larger than the first amount of the first measurement sample.

8. The method of claim 7, further comprising providing a sample supplier for supplying the measurement sample prepared by the sample preparation section to the flow cell, wherein
1) in the first operating mode, the controller controls the sample supplier so as to supply the first measurement sample to the flow cell for a first period; and
2) in the second operating mode, the controller controls the sample supplier so as to supply the second measurement sample to the flow cell for a second period longer than the first period.

9. The method of claim 8, wherein the controller controls the sample supplier so as to supply the measurement sample prepared by the sample preparation section to the flow cell at a predetermined speed, regardless of whether the controller is carrying out the first operating mode or the second operating mode.

10. The method of claim 7 further comprising providing a sample supplier for supplying the measurement sample prepared by the sample preparation section to the flow cell, wherein
1) in the first operating mode, the controller controls the sample supplier so as to supply the first amount of the first measurement sample to the flow cell; and
2) in the second operating mode, the controller controls the sample supplier so as to supply the second amount of the second measurement sample to the flow cell.

11. The blood analyzer of claim 7, wherein providing a detector comprises:

providing a light emitting section for irradiating light on the measurement sample passing through the flow cell; and providing a light receiving section for receiving light from the measurement sample irradiated by the light emitting section.

12. The blood analyzer of claim 7, wherein the controller controls the sample preparation section so as to prepare the measurement sample using substantially a similar amount of the reagent, regardless of whether the controller is operating the analyzer in the first operating mode or in the second operating mode.

13. A computer program product for enabling a computer to execute a blood analyzing method in a blood analyzer which is capable of performing analysis of blood, comprising:
   a computer readable medium including software instructions for enabling the computer to perform predetermined operations in a first operating mode or a second operating mode, the operations comprising:
   in the first operating mode, obtaining a first amount of an undiluted blood from a sample container, and preparing a first measurement sample of a first dilution ratio from the obtained undiluted blood and detecting blood components contained in a first amount of the first measurement sample;
   in the second operating mode, obtaining a second amount of the undiluted blood from a sample container, the second amount of undiluted blood being less than the first amount, and preparing a second measurement sample of a second dilution ratio higher than the first dilution ratio and detecting blood components contained in a second amount of the second measurement sample larger than the first amount of the first measurement sample.

14. The computer program product of claim 13, wherein
   in the first operating mode, detecting blood components comprises detecting blood cells contained in the first measurement sample for a first period, and
   in the second operating mode, detecting blood components comprises detecting blood cells contained in the second measurement sample for a second period longer than the first period.

15. The computer program product of claim 14 further comprising software instructions for supplying the measurement sample at a predetermined speed to a detector for detecting the analyte contained in the measurement sample, regardless of whether the measurement sample is from the first operating mode or the second operating mode.

16. The computer program product of claim 13, wherein detecting blood components comprises preparing measurement samples using a substantially similar amount of the reagent regardless of whether detecting blood components in the first operating mode or the second operating mode.

* * * * *